United States Patent
Tom

[19]

[11] Patent Number: 6,029,500

[45] Date of Patent: Feb. 29, 2000

[54] PIEZOELECTRIC QUARTZ CRYSTAL HYDROGEN SENSOR, AND HYDROGEN SENSING METHOD UTILIZING SAME

[75] Inventor: Glenn M. Tom, New Milford, Conn.

[73] Assignee: Advanced Technology Materials, Inc., Danbury, Conn.

[21] Appl. No.: 09/081,957

[22] Filed: May 19, 1998

[51] Int. Cl.[7] .......................... H01L 41/08; G01N 27/00; G01N 30/76; G08B 17/10

[52] U.S. Cl. .......................... 73/31.05; 73/24.06; 73/592; 73/24.01; 422/94; 310/313 R

[58] Field of Search ............... 73/24.01, 24.04, 73/31.05, 24.06, 29.01, 592, 597; 422/83, 90, 94; 310/313 R

[56] References Cited

U.S. PATENT DOCUMENTS

| | | | |
|---|---|---|---|
| Re. 35,544 | 7/1997 | Snow | 73/24.01 |
| 3,744,296 | 7/1973 | Beltzer | 73/24.01 |
| 4,056,803 | 11/1977 | White et al. | 340/15 |
| 4,163,384 | 8/1979 | Blakemore | 73/29 |
| 4,399,686 | 8/1983 | Kindlund et al. | 73/23 |
| 4,446,720 | 5/1984 | Sinclair | 73/23 |
| 4,637,987 | 1/1987 | Minten et al. | 436/151 |
| 4,730,478 | 3/1988 | Gedeon | 73/23 |
| 4,735,081 | 4/1988 | Luoma et al. | 73/23 |
| 5,037,624 | 8/1991 | Tom et al. | 423/210 |
| 5,042,288 | 8/1991 | Vig | 73/24.01 |
| 5,056,355 | 10/1991 | Hepher et al. | 73/24.03 |
| 5,065,140 | 11/1991 | Neuberger | 340/634 |
| 5,095,736 | 3/1992 | Fesler et al. | 73/23.2 |
| 5,117,146 | 5/1992 | Martin et al. | 310/313 R |
| 5,129,262 | 7/1992 | White et al. | 73/599 |
| 5,138,869 | 8/1992 | Tom | 73/31.03 |
| 5,151,110 | 9/1992 | Bein et al. | 55/75 |
| 5,151,395 | 9/1992 | Tom | 502/67 |
| 5,208,162 | 5/1993 | Osborne et al. | 436/6 |
| 5,221,871 | 6/1993 | Fuchs et al. | 310/313 R |
| 5,235,235 | 8/1993 | Martins et al. | 310/313 R |
| 5,235,844 | 8/1993 | Bonne et al. | 73/24.01 |
| 5,285,677 | 2/1994 | Oehler | 73/24.01 |

(List continued on next page.)

FOREIGN PATENT DOCUMENTS 6-308008  11/1994  Japan .

OTHER PUBLICATIONS

Neuburger, Glen G., "Detection of Ambient Hydrogen Chloride with a Zinc–Coated Piezoelectric Crystal Resonator Operating in a Frequency–Time Different Mode," Anal. Chem. 1989, 61, 1559–1563.

(List continued on next page.)

*Primary Examiner*—Hezron Williams
*Assistant Examiner*—J. David Wiggins
*Attorney, Agent, or Firm*—Steven J. Hulquist; Oliver A. M. Zitzmann

[57] ABSTRACT

A hydrogen sensor including a piezoelectric device with a hydrogen-interactive metal film that reversibly interacts with hydrogen to provide a correspondingly altered frequency response characteristic, relative to the frequency response in the absence of hydrogen. The piezoelectric device may be for example a quartz microbalance or a surface acoustic wave device, having a thin film (e.g., 10–100,000 Angstroms thickness) coating thereon of a hydrogen-interactive metal such as palladium, platinum, nickel or the like.

36 Claims, 10 Drawing Sheets

U.S. PATENT DOCUMENTS

| | | | |
|---|---|---|---|
| 5,320,817 | 6/1994 | Hardwick et al. | 423/237 |
| 5,323,636 | 6/1994 | McGowan et al. | 73/24.01 |
| 5,325,704 | 7/1994 | Mariani et al. | 73/24.06 |
| 5,325,705 | 7/1994 | Tom | 73/31.03 |
| 5,339,675 | 8/1994 | DiLeo et al. | 73/24.04 |
| 5,385,689 | 1/1995 | Tom et al. | 252/194 |
| 5,411,709 | 5/1995 | Furuki et al. | 422/91 |
| 5,417,821 | 5/1995 | Pyke | 204/153.1 |
| 5,445,008 | 8/1995 | Watcher et al. | 73/24.06 |
| 5,465,608 | 11/1995 | Lokshin et al. | 73/24.01 |
| 5,476,002 | 12/1995 | Bowers et al. | 73/24.01 |
| 5,518,528 | 5/1996 | Tom et al. | 95/103 |
| 5,573,728 | 11/1996 | Loesch et al. | 422/90 |
| 5,661,226 | 8/1997 | Bowers et al. | 73/24.01 |
| 5,705,399 | 1/1998 | Larue | 436/501 |
| 5,719,324 | 2/1998 | Thundat et al. | 73/24.01 |
| 5,795,993 | 8/1998 | Pfeifer et al. | 73/24.01 |
| 5,844,125 | 12/1998 | Pillion | 73/29.01 |
| 5,852,229 | 12/1998 | Josse | 73/24.06 |

OTHER PUBLICATIONS

Levenson, Leonard L., "II. Chemisorption on Single Element Thin Films," in *Applications of Piezoelectric Quartz Crystal Microbalances,* C. Lu, editor, vol. 7, Elsevier, Amsterdam, 1984, pp. 198–203.

"The World's First 8–Bit RISC MCU in an 8–Pin Package," Microchip Technology, Inc., Jun. 29, 1997, 2 pgs.

"SA612A Double–balanced mixer and oscillator," Phillips Semiconductors, Nov. 7, 1997, 12 pgs.

PIEZOELECTRIC QUARTZ CRYSTAL HYDROGEN SENSOR, AND HYDROGEN SENSING METHOD UTILIZING SAME

BACKGROUND OF THE INVENTION

1. Field of the Invention

This invention relates generally to a gas sensor for detecting the presence of hydrogen in gas streams or environments comprising same, as well as to an appertaining methodology for sensing the presence of hydrogen gas in such gas streams or environments.

2. Description of the Related Art

About one-half of all the sensors used to measure hazardous gases measure hydrogen. The bulk of these systems utilize as the detector element a Group VIIIB metal element (Ni, Pd, Pt) that is heated to catalytically oxidize the hydrogen, with the resulting change in heat load being the measured parameter for determination of the presence of hydrogen.

Sensors of such "hot wire" type have cross-sensitivity to other easily oxidized materials, such as alcohols and hydrocarbons. Such easily oxidized materials are common components of gases in a semiconductor manufacturing environment, and in such application the result is frequent occurrence of false alarms.

Since the current generation of hot wire sensors require an oxidation reaction for operation, such sensors are unable to detect hydrogen when it is present in inert gas streams or environments which are not of a character to support oxidative reaction. This is a severe deficiency of such hot wire sensors and limits their applicability and utility.

It would be a significant advance in the art to provide a sensor overcoming the aforementioned deficiencies of current hot wire sensors.

It therefore is an object of the present invention to provide a sensor system that is sensitive to the presence of hydrogen in the gas being monitored, and does not sense the presence of other oxidizable compounds, and which additionally is operable to sense the presence of hydrogen in inert gases or gas streams or environments that do not support oxidization.

Other objects and advantages of the present invention will be more fully apparent from the ensuing disclosure and appended claims.

SUMMARY OF THE INVENTION

The present invention relates to a high sensitivity, high selectivity hydrogen gas sensor that is usefully employed in environments including those that have posed difficulties in use of prior art hot wire sensors, namely, in gases containing other oxidizing species as well as in inert gases.

The invention in one aspect relates to a hydrogen gas sensor, comprising:

- a piezoelectric device that is electrically excitable to exhibit a frequency response;
- a metal layer on a surface of the piezoelectric device that in exposure to hydrogen gas reversibly interacts therewith to change the frequency response of the piezoelectric device; and
- means for outputting the frequency response change indicative of the presence of hydrogen gas.

The metal layer used in the piezoelectric device of the invention may for example comprise a metal selected from those of Group VIII of the Periodic Table (i.e., selected from nickel, palladium, platinum, cobalt, rhodium, iridium, iron, ruthenium and osmium). Preferably, such metal is selected from nickel, palladium, platinum and iridium, and more preferably from nickel, palladium and platinum, with palladium being a most preferred single metal species. The foregoing metal species may be utilized in combination with one another, e.g., as alloys or blends of two or more of such metals, or a metal of such type may be used in combination, e.g., in an alloy blend or composite, with other materials.

The hydrogen gas sensor of the invention is effective for sensing hydrogen in air and in inert environments, including environments that are non-supportive of oxidation and in which hot wire sensors of the prior art would be useless. The gas sensor of the invention also is sensitive to and selective for hydrogen at all gas phase concentrations (from 0% to 100% $H_2$ by volume of the gas being monitored). The hydrogen gas sensor of the invention operates in a reproducible and repeatable manner, and is highly effectively in character.

In one aspect, the hydrogen gas sensor of the present invention may comprise a piezoelectric device such as a quartz microbalance (QMB) or a surface acoustic wave (SAW) device.

In instances where the sensor is operated in a gas medium containing other species such as water, acetone, isopropanol, etc. that are adsorbable on the sensor surface, a second sensor may be employed to provide information on the concentration of these other species, to compensate for such potential interfering species in the hydrogen detection operation.

In a specific embodiment, at least two piezoelectric hydrogen gas sensors are utilized in a sensor assembly. One piezoelectric device is coated with a thin layer of a hydrogen-interactive metal or alloy, such as palladium, platinum, iridium, nickel or an alloy thereof. A second piezoelectric device is coated with a non-hydrogen-interactive metal, such as gold. The piezoelectric devices in such assembly are arranged to be closely matched in their fundamental frequencies, temperature coefficients, and drift character, in the absence of hydrogen. The difference in frequency between the piezoelectric devices is self-compensating for changes in humidity and temperature since the frequencies of the respective piezoelectric devices (frequency response characteristics) will move in synchrony with one another. Only the presence of hydrogen will differentially shift the frequency response between the two piezoelectric devices.

Another aspect of the invention relates to a method of determining the presence of hydrogen gas in an environment, comprising contacting gas from the environment with a piezoelectric device including a metal layer which in exposure to hydrogen gas provides an altered frequency response relative to corresponding operation of the piezoelectric device when the environment contains no hydrogen gas.

Other aspects and features of the invention will be more fully apparent from the ensuing disclosure and appended claims.

DETAILED DESCRIPTION OF THE INVENTION, AND PREFERRED EMBODIMENTS THEREOF

The present invention is based on the discovery that metal films reversibly interactive with hydrogen can be used as coatings on piezoelectric quartz crystals, to provide an effective sensor for hydrogen gas.

The hydrogen gas sensor of the invention is sensitive to hydrogen in air or other oxic environments, as well as to hydrogen in inert environments (environments that do not support oxidation), such as nitrogen, argon, helium, etc. The hydrogen gas sensor of the invention is extremely sensitive to, and selective for, hydrogen. Such sensor achieves a major advance in the art over the use of hot wire sensors of the type described in the Background of the Invention section hereof. The disclosures of the following U.S. patent applications are hereby incorporated herein by reference, in their entireties:

U.S. patent application Ser. No. 09/042,698 filed Mar. 17, 1998 in the names of Gautam Bhandari and Thomas H. Baum for "Hydrogen Sensor Utilizing Rare Earth Metal Thin Film Detection Element, and Differential Optical Sensing Method for Detection of Hydrogen;"

U.S. patent application Ser. No. 08/678,572 filed Jul. 12, 1996 in the names of Glenn M. Tom and Cynthia A. Miller for "Piezoelectric End Point Sensor for Detection of Breakthrough of Fluid, and Fluid Processing Apparatus Comprising Same;"

U.S. patent application Ser. No. 08/679,258 filed Jul. 12, 1996 in the names of Glenn M. Tom and Cynthia A. Miller for "Piezoelectric Environmental Fluid Monitoring Assembly and Method;" and U.S. patent application Ser. No. 08/785,342 filed Jan. 17, 1996 in the names of Glenn M. Tom and Cynthia A. Miller for "Piezoelectric Sensor for Hydride Gases, and Fluid Monitoring Apparatus Comprising Same."

Figure 1:
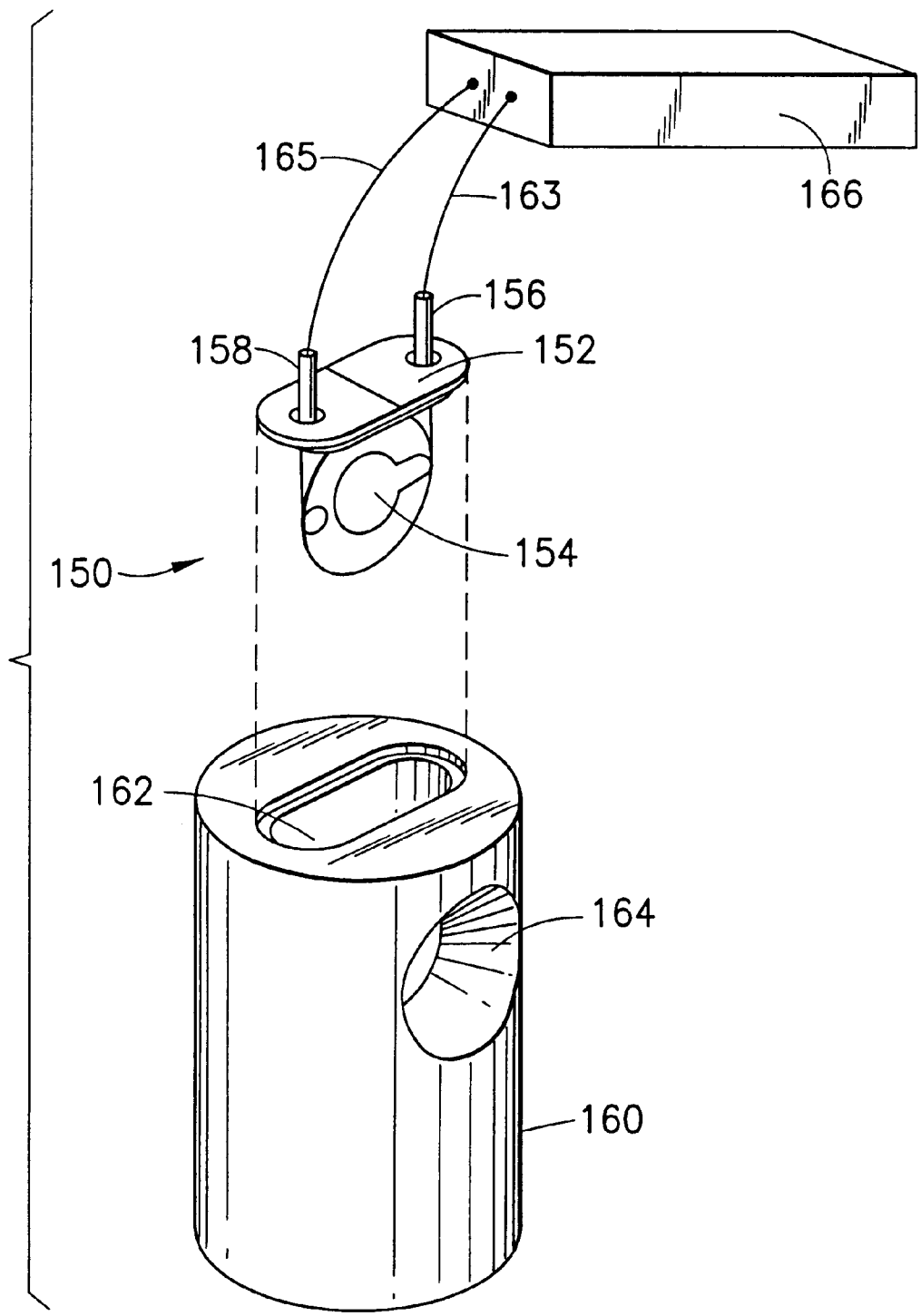
FIG. 1 is a schematic representation of a quartz microbalance, such as may be usefully employed in the practice of the present invention, in one embodiment thereof.

Referring now to the drawings, FIG. 1 is a schematic representation of a quartz microbalance device of a type that may be usefully employed in broad practice of the present invention as a hydrogen gas sensor.

FIG. 1 shows an exploded view of the sensor assembly, comprising a sensor element 150 and the housing 160. The sensor element 150 comprises a piezoelectric crystal 154 which is coated with a suitable hydrogen-interactive material, i.e., a material that interacts with hydrogen gas to yield an interaction product of different mass than the original material. The coated crystal is mounted on the plug member 152, with the respective leads of the piezoelectric crystal 154 protruding exteriorly of the plug member when the plug member is engaged with the housing 160, with the coated crystal extending into the cavity 162.

The material coated on the piezoelectric crystal 154 in accordance with the present invention comprises a metal film including one or more metals of Group VIII of the Periodic Table (i.e., nickel, palladium, platinum, cobalt, rhodium, iridium, iron, ruthenium and osmium) that is reversibly interactive with hydrogen gas to yield an interaction product of differing mass characteristic than the original metal film. By way of example, the metal film may contain nickel, palladium or platinum, or alloys including one or more of such metals, with which hydrogen gas will reversibly combine to form an interaction product of changed mass.

As a result of such changed mass, the frequency response characteristic of the coated piezoelectric crystal (when energized by suitable electrical excitation means) will be altered from the original frequency characteristics of the coated crystal (before contact and interaction with hydrogen gas in the fluid monitored). Such frequency change then may be used to generate a suitable output indicating the presence of hydrogen, as discussed more fully below.

The housing 160 features an opening 164 by which a gas can be flowed into the cavity 162 containing the sensor element 150. Although not shown in the front perspective view of FIG. 1, the housing 160 has another opening therein, opposite opening 164 and in register with such opening, for discharge from the housing of the gas flowed past the coated piezoelectric crystal. By this arrangement, the gas flow is directed to the coated piezoelectric crystal for hydrogen sensing.

The leads 156 and 158 of the sensor element may be coupled in circuit relationship to suitable electronics means shown schematically as electronics module 166 in FIG. 1, by which the presence and concentration of the hydrogen gas can be detected. The electronics module 166 is coupled to the sensor element leads 156 and 158 by wires 163 and 165, respectively.

Electronics module 166 may include electrical energy or power source means such as a battery, electrical connection means to a source of electrical current, or an electrical generator, which provides the requisite electrical energy (oscillating electrical field) for excitation of the piezoelectric crystal. Electronics module 166 additionally provides the functions of (i) sampling the output resonant frequency of the piezoelectric crystal while the oscillating electric field is applied thereto, (ii) determining the change in resonant frequency from the fundamental resonant frequency when the sensor material interacts with hydrogen in the fluid being monitored, and (iii) generating an output indicative of the presence of hydrogen in such fluid.

The output indicative of the presence of hydrogen in the fluid being monitored may comprise an alarm output, such as a flashing warning light or other visual alarm, a beeper, siren or other audible alarm, a buzzer, vibrator or other tactile means (as for example when the hydrogen gas sensor is embodied in a wearable unit with a body-mounted output device), etc. Alternatively, the output indicative of the presence of hydrogen in such fluid may comprise a strip-chart recorder or other continuous feed print-out means, a visual display interface providing data or readings generated by the electronics module based on the piezoelectric frequency response characteristics of the sensor unit, etc. Further, combinations of the aforementioned types of output means may be employed, and/or any other suitable displays, recorders, monitors, etc., including digital as well as analog types of output means.

In a specific embodiment of the hydrogen gas sensor assembly shown in FIG. 1, the housing 160 may comprise an aluminum housing which has the cavity 162 machined into it for the insertion of the sensor element, as well as two feedthrough (¼" NPT) openings (opening 164, and the opposite opening not shown in FIG. 1) for the gas to flow through the sensor. In the body of this housing is a flow restricting orifice. This ¼" aluminum housing may be readily coupled with front end driver electronics, that are plugged directly onto the legs (leads 156 and 158) of the sensor assembly. The resulting assembly may be coupled to a gas sensor tube or otherwise be joined in flow sensing communication with the gas stream or environment being monitored.

Figure 2:
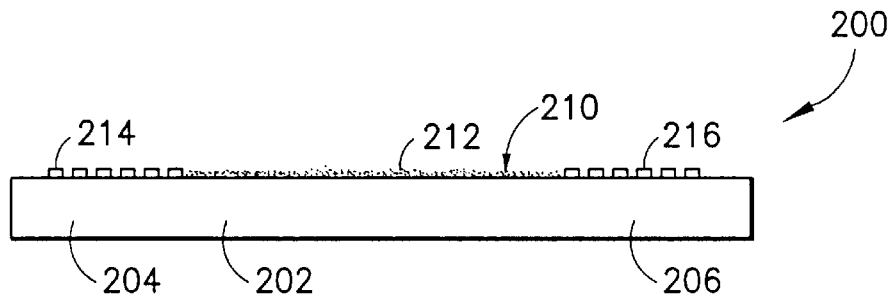
FIG. 2 is a side elevation view of a surface acoustic wave device, such as may be used in the practice of the present invention, according to another embodiment thereof.

FIG. 2 is a side elevation view of a surface acoustic wave device according to one aspect of the present invention, that may be used as a mass-sensitive element for the detection of hydrogen gas.

Figure 3:
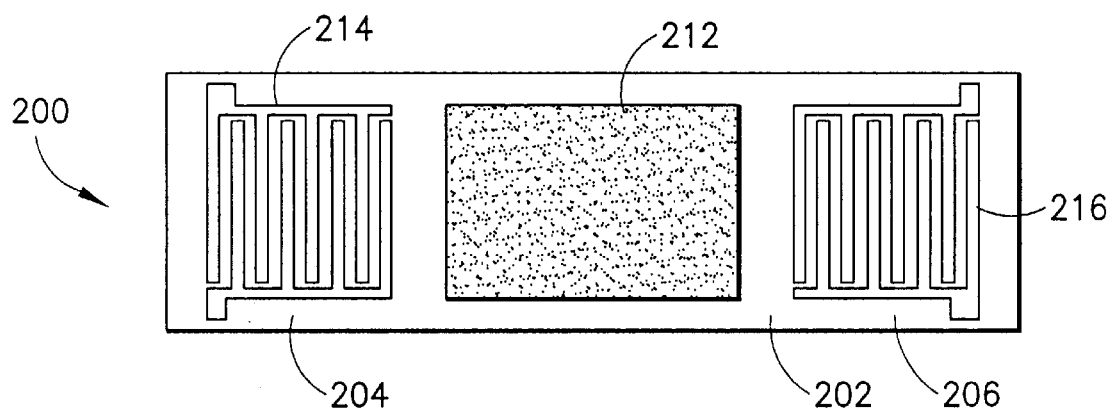
FIG. 3 is a top plan view of the surface acoustic wave device of FIG. 2.

The surface acoustic wave device 200 includes a quartz crystal 206 of thin rectangular character (as more fully shown in the top plan view of FIG. 3, wherein all parts are correspondingly numbered). The quartz crystal 202 includes a transmission end portion 204 and a reception end portion 206. End portion 204 is provided with an electrode structure 214, and end portion 206 is provided with electrode structure 216, on the top surface of the crystal. Electrode structures 214 and 216 (which in use are connected to an electronics module of a general type as described hereinabove in connection with FIG. 1) are separated by a central portion of the crystal surface having a coating thereon of containing hydrogen-interactive metal.

The transmitting electrode structure 214 is energized by a suitable electrical source (not shown) to generate acoustic waves on the surface of the quartz crystal 202 that are propagated to the receiving electrode structure 216, where the acoustic wave is sensed.

Hydrogen gas contacting the metal film 212 changes the acoustic wave velocity. The change is proportional to the number of molecules binding to the coated quartz crystal, which in turn is indicative of the presence and concentration of hydrogen in the environment or gas stream being monitored.

The hydrogen-interactive metal that may be utilized in the practice of the present invention, as a thin film coating on a quartz crystal in a quartz crystal microbalance, or on the surface of a quartz crystal utilized as a surface acoustical wave device, may comprise any suitable metal with which hydrogen is reversibly interactive to effect a change in mass of the metal material. Examples of such metals include nickel, palladium, platinum, cobalt, rhodium, iridium, iron, ruthenium, osmium, alloys containing two or more of the foregoing metals, and alloy compositions including one or more of such metals with other alloying species. Particularly preferred metal species include palladium, platinum and nickel. Palladium generally is a most preferred metal.

In accordance with one aspect of the invention, a multiplicity of sensors, e.g., quartz microbalance and/or surface acoustic wave sensors, may be deployed, having different coatings on respective ones of such devices, to provide correction for specific gas components or conditions, by use of associated comparator circuitry and/or computational means, e.g., microprocessors, programmable digital computers, or the like.

In this respect, multiple corresponding devices may be employed that have differential interactive character with hydrogen, if the associated microelectronics have sufficient resolution capability to provide appropriate correction and useful output. For example, different films may be employed on different mass-sensitive QMB or SAW devices in the practice of the present invention, where one of the coatings is highly selective for hydrogen while another one of the coatings, on another mass-sensitive device, is noninteractive with hydrogen but otherwise displays same or similar characteristics to other process conditions and gas components that may be present. In such instance, the differential frequency response between the respective films may be utilized to provide a corrected output reflecting the presence or concentration of hydrogen gas.

The hydrogen gas sensor of the present invention has the benefit that it is sensitive across the entire range of concentration of hydrogen (from 0% to 100% $H_2$ by volume) in the fluid being monitored.

In some embodiments, it may be desirable to provide the hydrogen gas sensor of the invention with associated gas flow directing or channeling means, such as an aspirator, ejector, eductor, side stream diverter, flow channel, flow accumulator vessel, etc., so that the fluid to be monitored, e.g., ambient air in an environment susceptible to hydrogen leakage or contamination, may be monitored most effectively.

Figure 4:
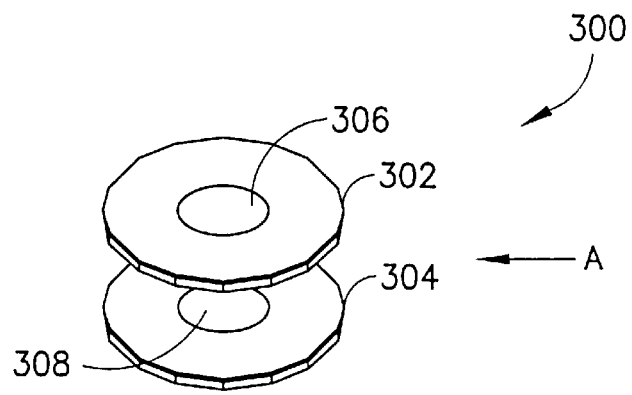
FIG. 4 is a schematic depiction of quartz microbalance elements including one crystal with palladium electrodes and one crystal with gold electrodes, shown in relation to a gas flow direction for the sensing operation.

FIG. 4 is a schematic representation of an assembly 300 of quartz microbalance elements 302 and 304, which are aligned with the gas flow direction (indicated by arrow A), to sense the presence of hydrogen in the gas flow stream contacted with the quartz microbalance elements.

Quartz microbalance element 302 includes a quartz crystal having deposited thereon an electrode coating 306 of palladium. The other quartz microbalance element 304 comprises a quartz crystal having deposited thereon an electrode coating 308 of gold.

As the gas stream is flowed in direction A past the quartz microbalance elements and the palladium electrode 306 and gold electrode 308, any hydrogen present in the gas stream will physically adsorb on and solubilize in the palladium electrode coating, but will not appreciably adsorb on or solubilize in the gold electrode coating.

In response to electric energy inputted to such crystals, the quartz crystal will generate output signals whose differential character is attributable the presence of hydrogen, which will shift the frequency response of the quartz crystal 302 including the palladium electrode 306, in relation to the frequency response of the quartz crystal including the gold electrode 308.

As discussed hereinabove, the metals that are potentially useful in the practice of the invention to reversibly interact with hydrogen include Group VIII metals and most favorably Ni, Pd and Pt. Alloys of two or more of these metals may also be employed, as well as alloys containing one or more of these metals with other alloying species.

For the reference electrodes, inert metals such as Cr, Ag, Au, etc. are potentially useful materials of construction.

The hydrogen-interactive metal films used in the practice of the present invention may be deposited on the quartz crystal substrate by any suitable method, such as by solution deposition, electroplating, sputtering, chemical vapor deposition, or any other suitable methodology, by which a film of appropriate characteristics is formed on the substrate.

As a specific example, the hydrogen-interactive metal may be formed on the substrate by chemical vapor deposition from a corresponding source reagent precursor. In the case of palladium as the hydrogen-interactive metal, useful precursors for chemical vapor deposition include palladium bis(hexafluoroacetylacetonate), diallyl palladium, and allyl cyclopentadienyl palladium. For platinum, as another example of a hydrogen-interactive metal, useful precursors are more fully described in U.S. patent application Ser. No. 08/673,372 filed Jun. 28, 1996 in the names of Thomas H. Baum, Peter S. Kirlin and Sofia Pombrik for "Platinum Source Compositions for Chemical Vapor Deposition of Platinum," the disclosure of which hereby is incorporated by reference in its entirety.

In general, the thickness of the hydrogen-interactive metal layer on the quartz crystal substrate may be any suitable thickness providing sufficient sensitivity and responsivity to hydrogen. Typically, hydrogen-interactive metal films of thicknesses of from about 10 to about 100,000 Å may be usefully employed, with preferred film thicknesses being on the order of from about 20 to about 2000 Å, and most preferably from about 50 to about 500 Å in thickness.

The hydrogen gas sensors of the invention are highly effective in monitoring the presence as well as concentration of hydrogen in an environment. For example, the concentration of hydrogen in the gas being monitored by the sensor may be established by quantitation of the frequency response characteristics of the piezoelectric element used in the hydrogen gas sensor, to provide a corresponding output indicative of the concentration of the hydrogen gas in the fluid environment being monitored.

The metal films utilized in hydrogen gas sensors of the present invention are reversibly interactive with hydrogen gas, and thus are distinguishable from hydrogen gas detectors in which the detection element comprises a material with which hydrogen is chemically reactive to form a reaction product by irreversible chemical reaction. Although a number of metals are reactive with hydrogen, such metals in many cases are also highly reactive with oxygen. An example is barium, which reacts with hydrogen gas to form barium hydride, but is also highly reactive with oxygen to form barium oxide, and is reactive with nitrogen to form barium nitride. Accordingly, although barium forms a reaction product of changed mass characteristic relative to the reactant starting material (elemental barium metal), such metal would be wholly useless for detecting hydrogen in an ambient air environment or nitrogen gas stream. The same is true of many other metal species. The metals utilized in the hydrogen gas sensor of the present invention, however, are those which reversibly interact with hydrogen gas.

The hydrogen gas sensors of the present invention may be utilized in systems or instances in which hydrogen is employed as a fuel, reactant, carrier gas, etc, to provide a safe and effective means for detection of hydrogen leakage or to regulate the amount of hydrogen in a gas stream or environment containing same. For example, the hydrogen sensor of the invention may be utilized in proximity to hydrogen storage facilities, to ensure that ambient hydrogen is below a concentration presenting a deflagration condition.

Further, the hydrogen gas sensors of the present invention may be utilized at varying temperature conditions with appropriate calibration, since the interaction of hydrogen with the hydrogen-interactive metal will vary as a function of temperature.

The hydrogen-interactive metals utilized in the sensors of the invention have the following advantages:

1. Such hydrogen-interactive metals do not respond to simple hydrocarbons. As mentioned hereinabove, current hot-wire detectors burn hydrogen and measure the differential heat load. Other hydrocarbons burn as well giving false readings. The hydrogen gas sensor of the present invention weakly physically adsorbs the hydrogen on a low surface area film, with which "neutral" sensors (or reference sensors) having the same weak physical sorption characteristics may be employed to provide reliable compensation.

2. The hydrogen gas sensor of the present invention will operate effectively in both oxygen-rich and oxygen-poor environments, unlike current hot-wire sensors.

3. Since the temperature of the hydrogen gas sensor is low in relation to hot-wire sensors of the prior art, power requirements are correspondingly reduced.

A multiplicity of quartz microbalance detectors of the invention may be utilized with one another to form a detector system, as discussed hereinabove, in which for example a palladium electrode coating on the quartz microbalance would exhibit hydrogen, water, aging and temperature effects. A corresponding gold electrode coated quartz microbalance utilized in association with the palladium electrode quartz microbalance would cancel out the water, aging and temperature effects.

The features and advantages of the invention are more fully illustrated by the following non-limiting examples, wherein all parts and percentages are by weight, unless otherwise expressly stated.

EXAMPLE 1

A quartz microbalance with Pd electrodes (1000 Å thick, both electrodes) was exposed to $H_2$ at room temperature at 1, 2, 3, and 4% levels in air. The response curve is shown in FIG. 5.

The horizontal lines are the states at 1, 2, 3, and 4%. The hydrogen gas sensor was moved through the following sequence:

$$0\% \rightarrow 1\% \rightarrow 2\% \rightarrow 3\% \rightarrow 4\% \rightarrow 3\% \rightarrow 2\% \rightarrow 1\% \rightarrow 0 \rightarrow$$

Figure 5:
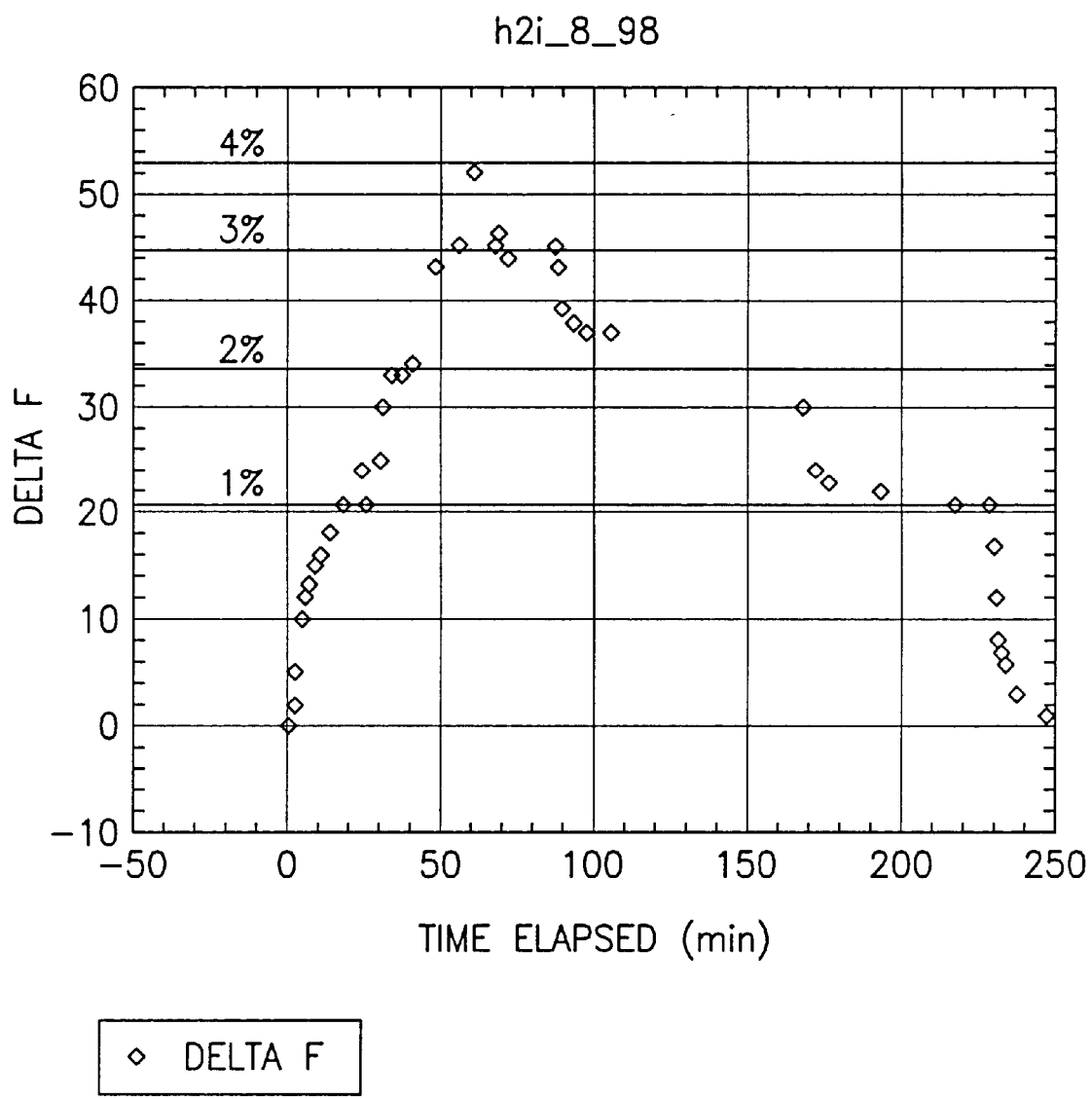
FIG. 5 is a plot of the change in frequency as a function of time for a quartz microbalance with palladium electrodes exposed to hydrogen at room temperature, at varying concentrations in air.

The graphical data of FIG. 5 show that the response of the quartz microbalance to $H_2$ is rapid and reversible.

When the Pd quartz microbalance is exposed to hydrogen, hydrogen gas dissolves in the metal film, adds mass to the system and a frequency shift is observed.

$$Pd + H_2 = Pd/H$$

$$\Delta F = \alpha \Delta m$$

wherein:

$\Delta F$ is the change in frequency, $\alpha$ is a coefficient for the specific system, and $\Delta m$ is the change in mass.

A corresponding experiment was carried out wherein the quartz microbalance was exposed to nitrogen and 100% hydrogen. The change in frequency was estimated to be approximately 400 Hertz.

In the testing from which the data of FIG. 5 were generated, the quartz microbalance after exposure to the specified percentage of hydrogen was equilibrated at such level, and the sensor then was stepped down to zero percent hydrogen, following which the next succeeding concentration level of hydrogen was established.

EXAMPLE 2

The same quartz microbalance as used in Example 1 was evaluated for frequency response as a function of percent hydrogen in the gas being contacted with the microbalance.

Figure 6:
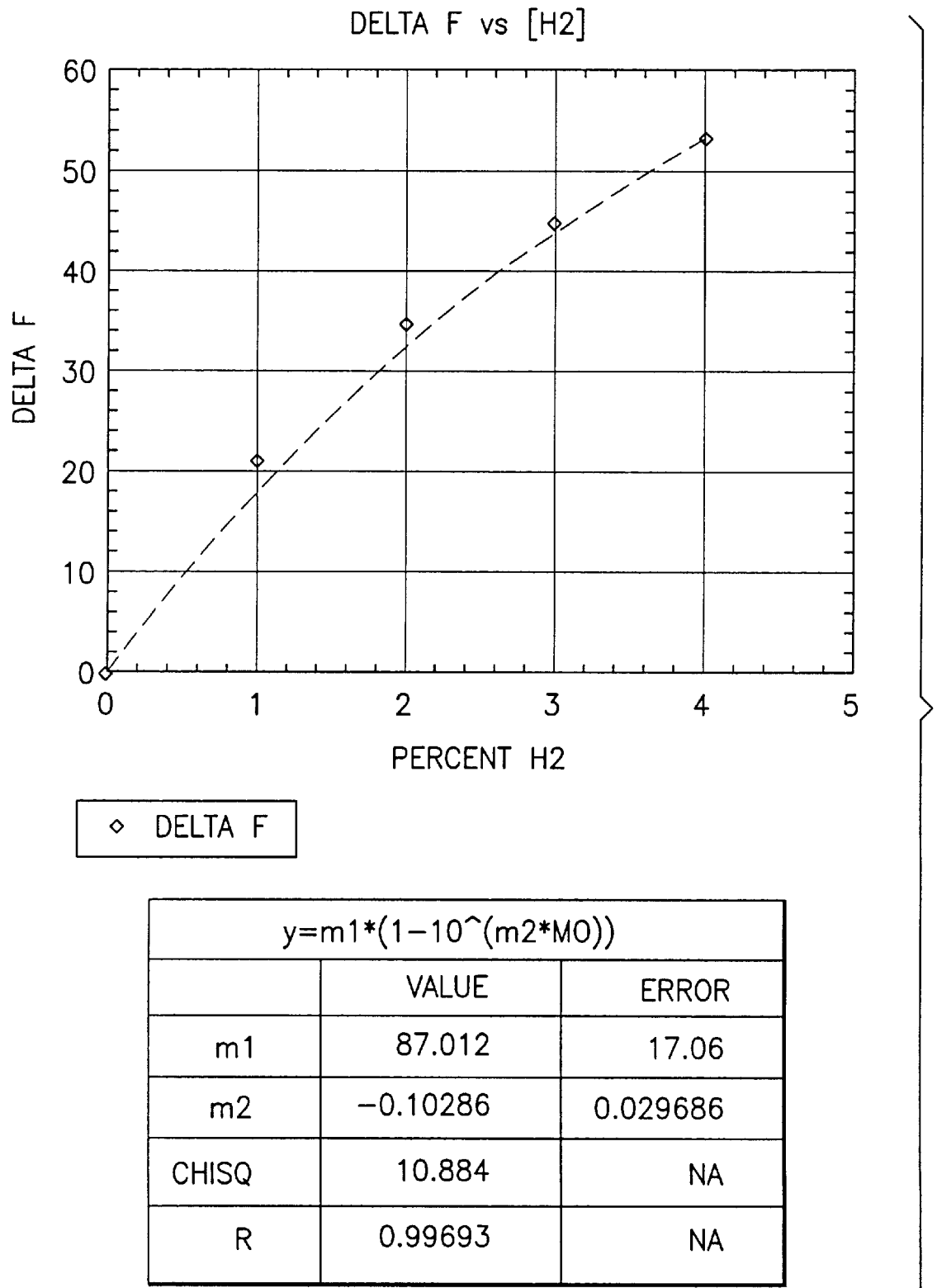
FIG. 6 is a plot of the change in frequency of a quartz microbalance including a crystal coated on both sides with palladium, in exposure to hydrogen, as a function of percent hydrogen in the gas environment being monitored.

FIG. 6 is a plot of the frequency response, showing a high sensitivity to change in the amount of hydrogen present in the gas being monitored.

The data shown in FIG. 6 can be fit to the following equation:

$$\Delta F = F - F_o = 87 Hz * (1 - 10^{-0.1 * [H2]})$$

where $F_o$ is the base frequency.

The fit of the data and foregoing equation is good.

The foregoing data indicate that Pd will respond to hydrogen in the presence of air at room temperature, and Pd will respond without hysteresis.

A 1000 Å thick Pd coating has very high sensitivity to $H_2$. The coating could be much thinner and still have sufficient sensitivity.

A 1000 Å thick Pd coating is fast to respond to $H_2$. A thinner coating will have a still faster response time.

The optimum coating thickness in a given application of the invention will balance the foregoing considerations of response speed and sensitivity considerations, and may for example be on the order of from about 100 to about 500 Å in thickness. The specific desired thickness in a given end use application will depend among other factors on the specific hydrogen-interactive material, the microelectronics associated with the quartz microbalance, and the gas composition being monitored for the presence of hydrogen.

EXAMPLE 3

Figure 7:
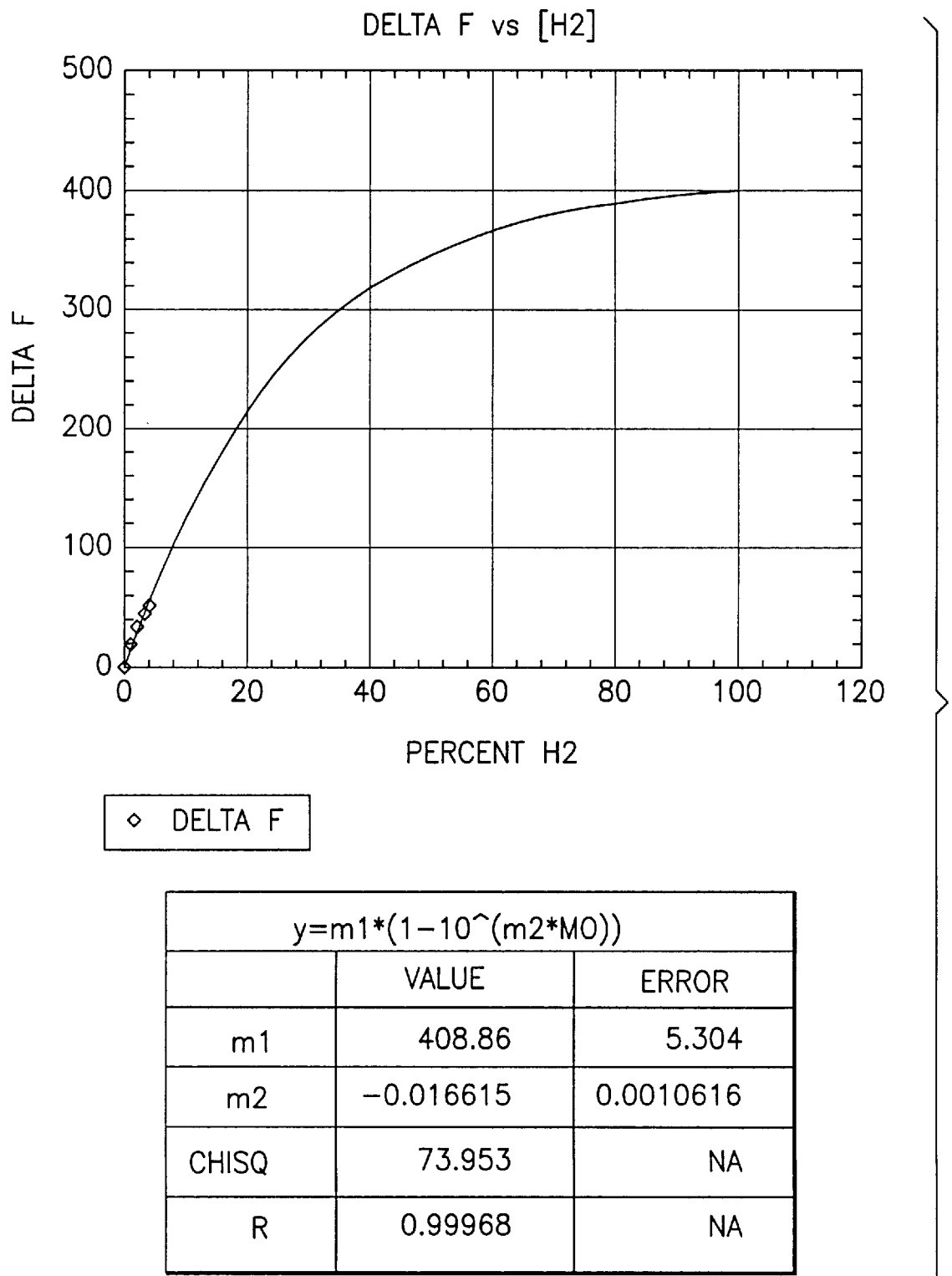
FIG. 7 is a plot of frequency change as a function of percent hydrogen, for a quartz microbalance with palladium electrodes, exposed to hydrogen gas.

The same quartz microbalance as in Example 1 was exposed to 100% $H_2$. A frequency shift of about 400 Hz was found. If the 400 Hz point for pure hydrogen is inserted into the data set, the fitting curve is shown in FIG. 7, showing frequency change as a function of percent hydrogen.

EXAMPLE 4

A palladium electrode coated quartz microbalance was tested in hydrogen detection service, to gauge the hydrogen response characteristics of the microbalance in air and nitrogen, to determine the effects of temperature and water, and cross terms of the foregoing parameters, as well as to assess thickness effects for the electrode coating.

The results are set out below.

Description of M4, M8, and OFAT Experiments

The M4 and M8 tests are a designation of the Taguchi statistical design of experiments. In an M4 experiment, 4 experiments are run with 2 variables at 2 levels. The M4 will yield the first order effects of the two variables and the cross term. The M8 will add another variable (3 altogether). The M8 yields the 3 first order, 3 cross terms, and a noise estimate.

The OFAT (One Factor At a Time) test was also utilized.

Experiments were carried out with constant water and temperature to gauge the effect of hydrogen concentration in air and nitrogen background gas.

The M8 data were generated from 2 levels of temperature (28 and 35° C.), water (3000 and 8000 ppm), and hydrogen (1 and 3.5%). Typical data are set out below in Table 1.

TABLE 1

| M8 Results | |
|---|---|
| Temperature (T) | 3.5 |
| Concentration (C) | 86 |
| Humidity (H) | −2.5 |
| T × C | 8.5 |
| T × H | 0 |
| C × H | 2.5 |
| Noise | 0 |

The first column shows the names of the three primary effects, the cross terms and the noise. The second column shows the size of the various effects. The bigger the absolute number, the more important the effect.

These data show that the term having the primary effect is the concentration of hydrogen. The other effects are much smaller.

Figure 8:
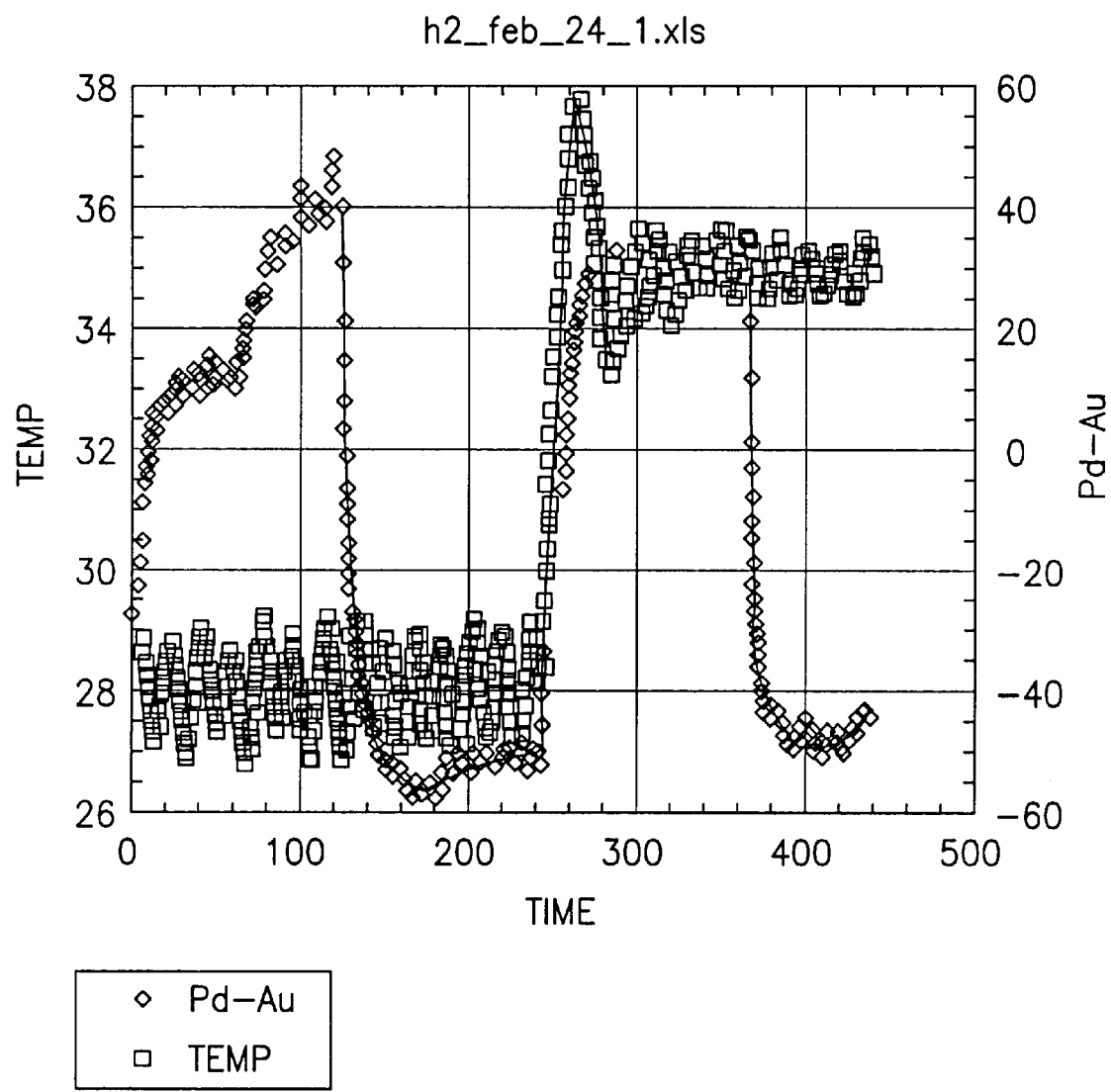
FIG. 8 is a plot of temperature and quartz microbalance performance as a function of time.

The raw data are shown in FIG. 8. Each of the steps was 60 minutes long.

One of the effects observed in this study was the rise in the frequency at 28° C., 1% $H_2$, 3000 to 8000 ppm $H_2O$. This effect is found in the C×H cross term.

When hydrogen was omitted or when nitrogen was substituted for air, this frequency rise was not observed. Further, at higher hydrogen concentration levels or higher temperatures, this effect was minimized.

An M4 data set generated at 35° C. is set out in Table 2 below and shows that concentration of hydrogen is the major effect. The concentration of water and the cross product are quite small.

TABLE 2

| M4 Results | |
|---|---|
| Concentration (C) | 77.98 |
| Humidity (H) | −3.28 |
| C × H | −2.72 |

EXAMPLE 5

Figure 9:
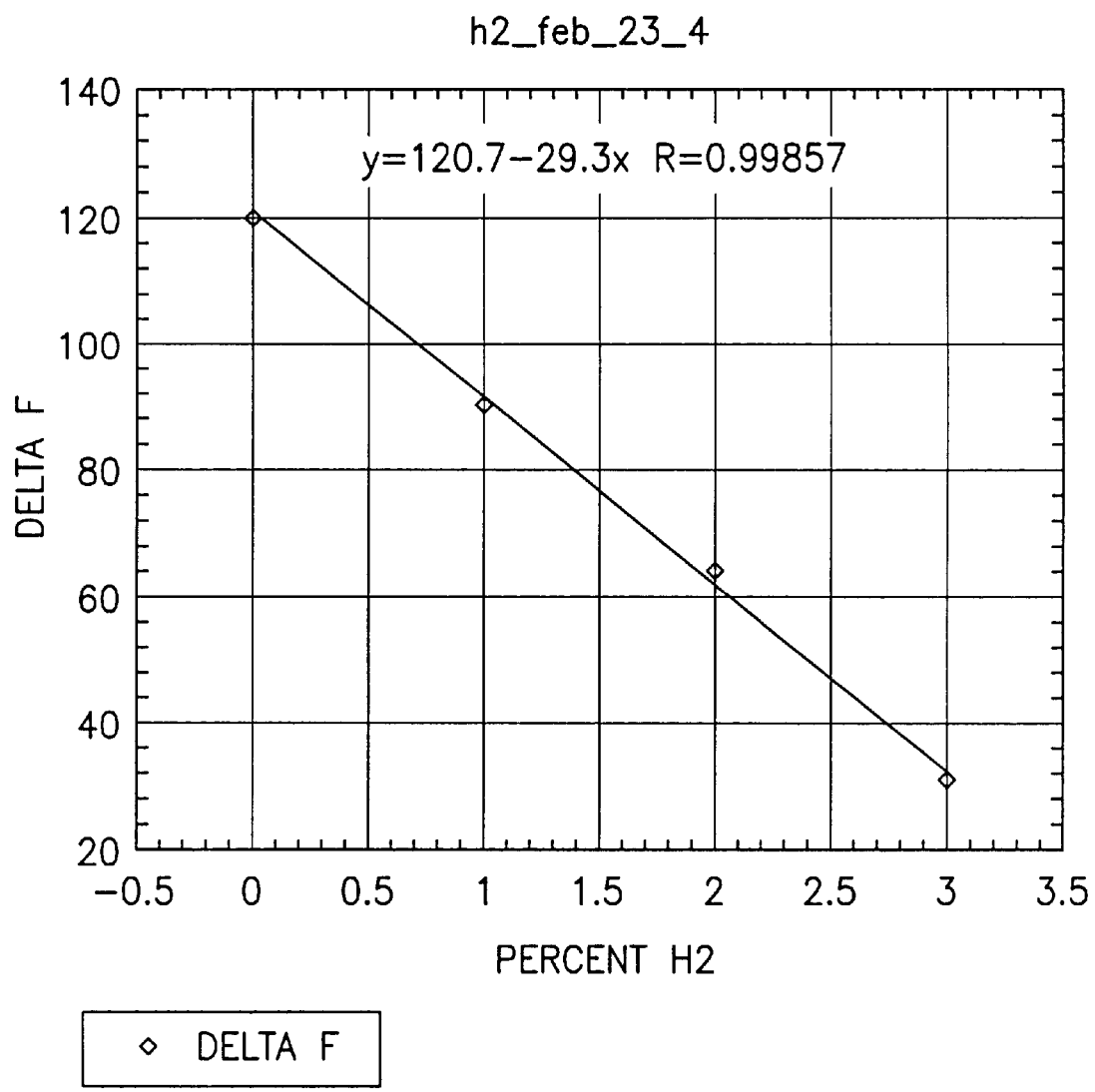
FIG. 9 is a plot of change in frequency as a function of hydrogen percentage in air, for a quartz microbalance, in air at 28° C., having a 250 Angstroms thick coating of palladium thereon.
Figure 10:
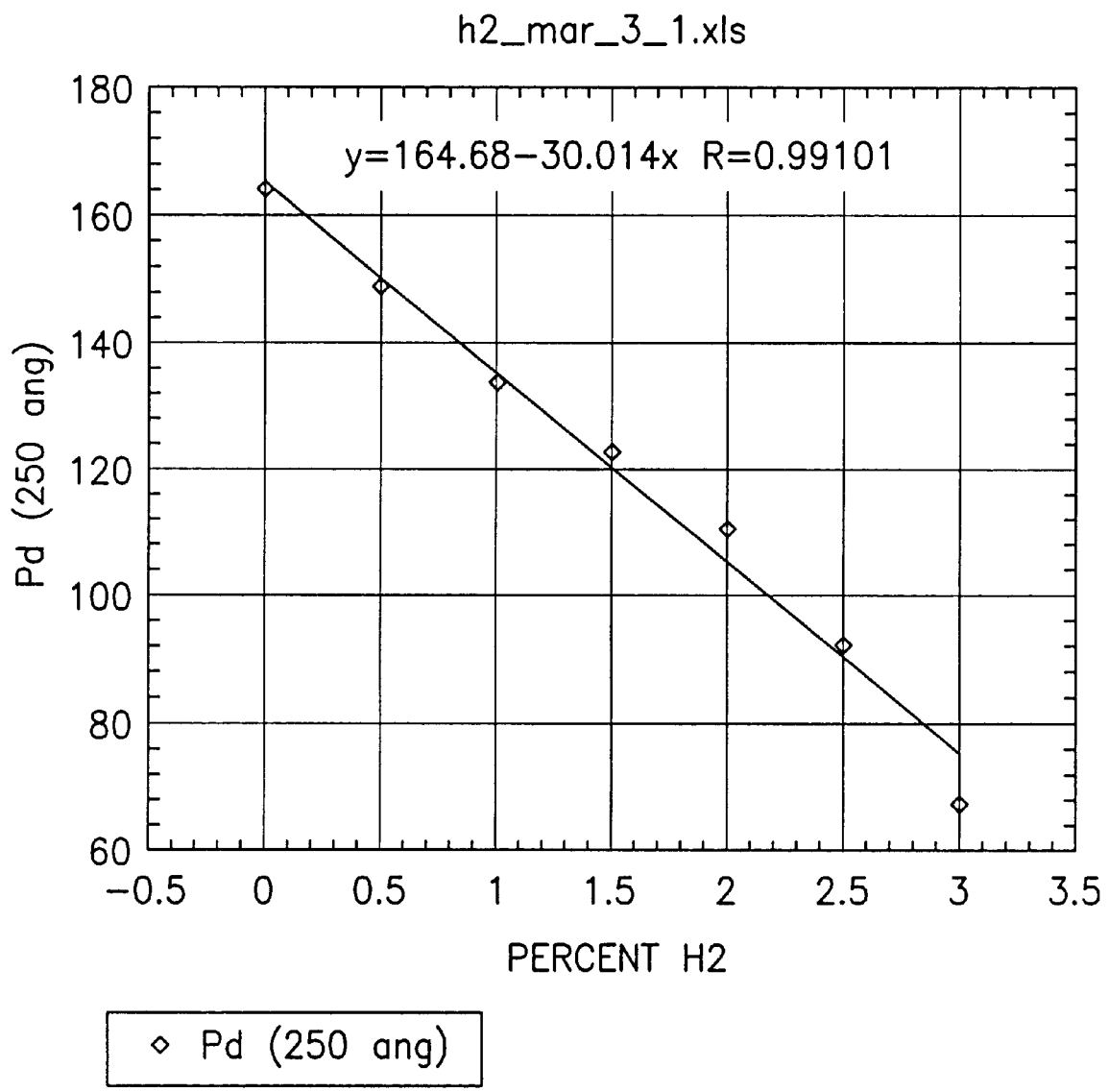
FIG. 10 is a plot of frequency change as a function of hydrogen percentage for a quartz microbalance having a 250 Angstroms thick coating of palladium thereon, in nitrogen gas at 35° C.

Two calibration curves are shown in FIGS. 9 and 10 for a quartz crystal microbalance having a 250 Å electrode coating of palladium thereon. Data were measured on the quartz microbalance in air at 28° C. and in nitrogen at 35° C., respectively. The slopes shown in the plots of FIGS. 9 and 10 are virtually identical, at approximately 30 hertz/ percent $H_2$.

EXAMPLE 6

Figure 11:
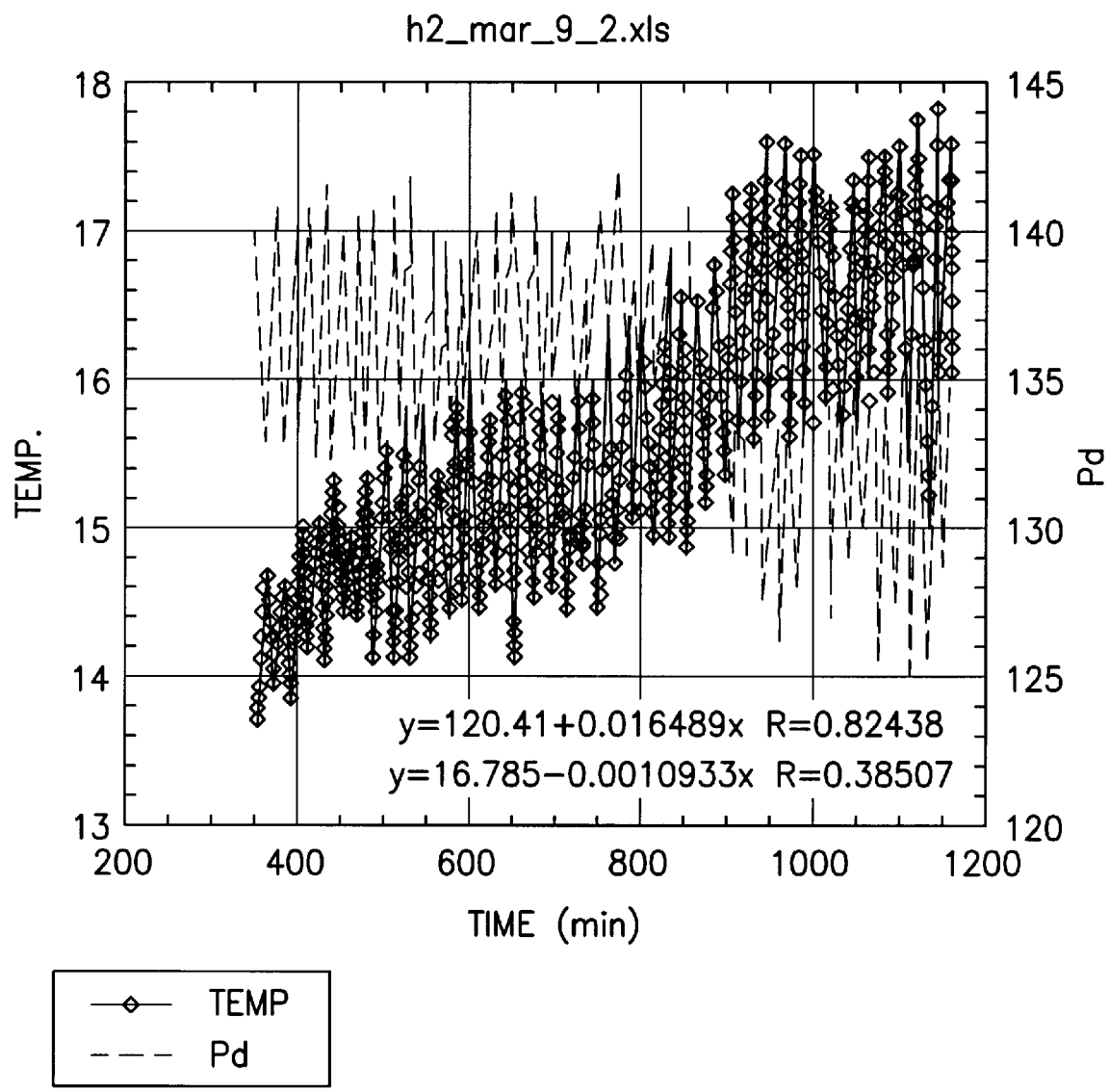
FIG. 11 is a plot of the frequency response of a 250 Angstroms thick palladium coating on a quartz microbalance suspended in room air as a function of temperature and time.

The frequency response characteristics were determined for a quartz microbalance including a 250 Å thick palladium electrode coating that was suspended in room air. The frequency response was measured as a function of the temperature. The results are shown in FIG. 11.

The results indicated that the temperature coefficient for the quartz crystal microbalance was on the order of 16 Hz/°C.

EXAMPLE 7

An experiment was conducted with quartz crystal microbalances. One quartz microbalance had a palladium electrode coating at a thickness of 250 Angstroms, and the other quartz microbalance had a palladium electrode coating with a thickness of 1000 Angstroms.

The rate of diffusion in the quartz microbalance electrode metal film is governed by the Einstein equation:

$$d = t^2/D$$

wherein:

d is the diffusional distance;

t is the time during which diffusion occurs; and

D is the diffusion coefficient.

According to this equation, the time to diffuse a distance 2d is four times longer than the time required to diffuse a distance d.

This diffusion equation provides that the rate of equilibration will be 16 times faster for the 250 Angstroms thick palladium coating than for the 1000 Angstroms thick palladium coating.

Figure 12:
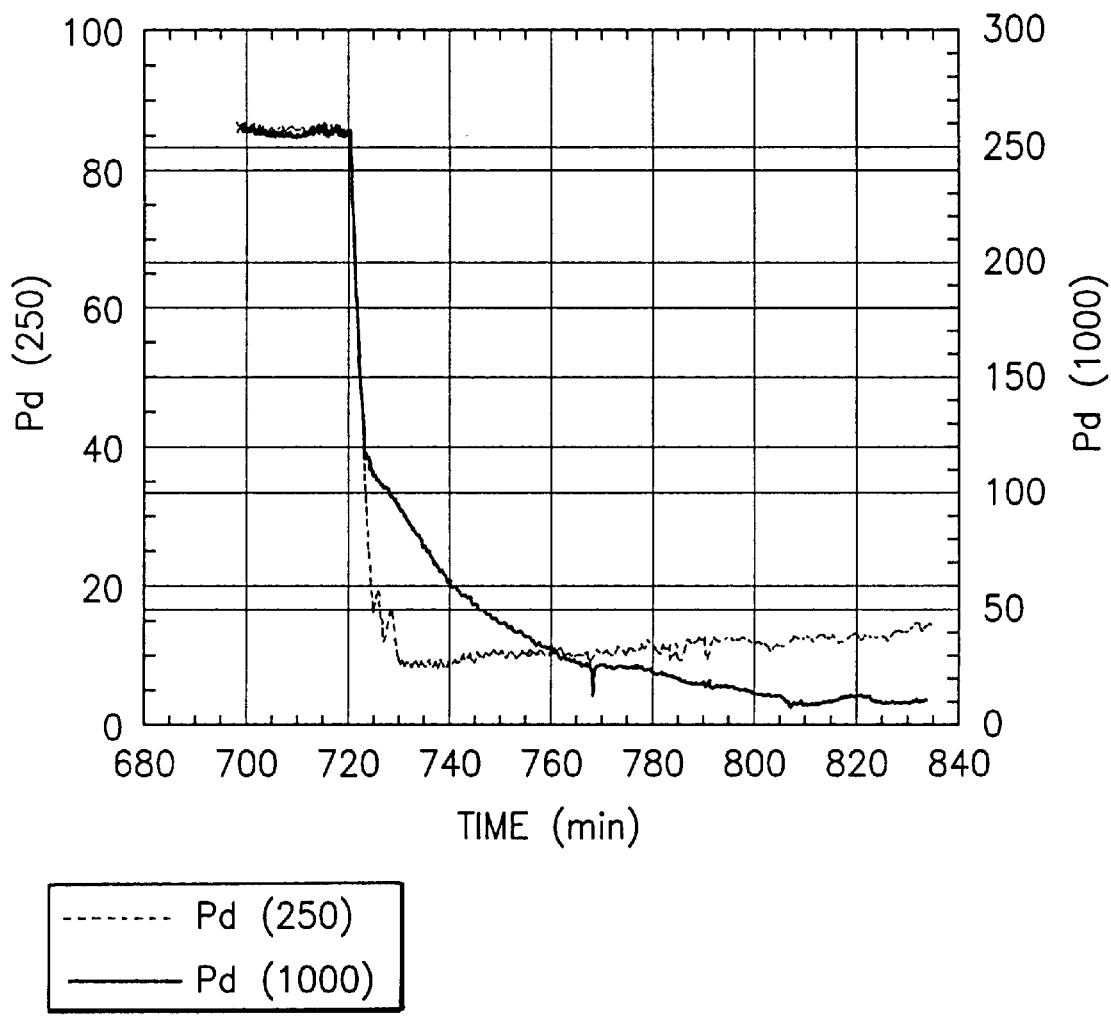
FIG. 12 is a graph showing the speed of response of 250 Angstroms thick and 1000 Angstroms thick palladium electrode coatings on a quartz microbalance.

The data for a transition are plotted in FIG. 12 and show the speed of response of 250 Å thick and 1000 Å thick palladium electrode coatings on a quartz crystal microbalance.

The step change was 1% to 3.5% Hz, 8000 ppm to 3000 ppm $H_2O$, and 28° C. to 35° C. The balance of the gas was nitrogen. The thickness of the palladium coating was determined by measurement of the manufacturer of the quartz crystal microbalance, International Crystal Manufacturing Co.

It can be seen from FIG. 12 that the thicker (1000 Angstroms thick) coating is indeed slower than the thinner (250 Angstroms thick) coating. The factor of 16 predicted by the Einstein diffusion equation was not observed; the empirical value was closer to 10. The change in frequency was 75 Hz for the 250 Angstroms thick coating, versus 250 Hz for the 1000 Angstroms thick coating. If the frequency change ratio reflects a true thickness ratio, the value of the thickness ratio is equal to 3.3. With such true thickness ratio, the associated response time characteristics are rendered more consistent with the Einstein diffusion equation.

A coating thickness of approximately 250 Angstroms provides good response characteristics. The 1000 Angstroms thick coating responded much more quickly than the lower thickness coating, but at 250 Angstroms coating thickness, the sensitivity of the film will be high (about 30 Hz/% $H_2$) and drift effects will be minimized.

While the invention has been described herein with reference to specific aspects, features, and embodiments, it will be apparent that other variations, modifications, and embodiments are possible, and that all such variations, modifications, and embodiments therefore are to be regarded as being within the spirit and scope of the invention.

I claim:

1. A hydrogen gas sensor, comprising:

a piezoelectric device that is arranged for contacting gas from a monitored environment to detect the presence of hydrogen therein and that is electrically excitable to exhibit a frequency response;

a metal layer on a surface of the piezoelectric device that in exposure to hydrogen gas reversibly interacts therewith to change the frequency response of the piezoelectric device; and means for outputting the frequency response change indicative of the presence of hydrogen gas.

2. A hydrogen gas sensor according to claim 1, wherein the metal layer comprises one or more metal species selected from the group consisting of nickel, palladium, platinum, cobalt, rhodium, iridium, iron, ruthenium and osmium.

3. A hydrogen gas sensor according to claim 1, wherein the metal layer comprises a metal species selected from the group consisting of palladium, platinum, nickel, alloys of two or more of the foregoing metals, and alloys containing one or more of the foregoing metals with other metal species.

4. A hydrogen gas sensor according to claim 1, wherein the metal layer comprises palladium.

5. A hydrogen gas sensor according to claim 1, wherein the piezoelectric device comprises a quartz microbalance.

6. A hydrogen gas sensor according to claim 1, wherein the piezoelectric device comprises a surface acoustic wave device.

7. A hydrogen gas sensor according to claim 1, wherein the thickness of the metal layer is from about 10 to about 100,000 Å.

8. A hydrogen gas sensor according to claim 1, wherein the thickness of the metal layer is from about 20 to about 2000 Å.

9. A hydrogen gas sensor, comprising:

a piezoelectric device comprising a quartz microbalance having a palladium electrode coating thereon, said piezoelectric device being arranged for contacting gas from a monitored environment to detect the presence of hydrogen therein and being electrically excitable to exhibit a frequency response;

a metal layer on a surface of the piezoelectric device that in exposure to hydrogen gas reversibly interacts therewith to change the frequency response of the piezoelectric device; and means for outputting the frequency response change indicative of the presence of hydrogen gas.

10. A hydrogen gas sensor according to claim 1, further comprising a second piezoelectric device of corresponding type but lacking a hydrogen-interactive metal layer, and constructed and arranged to provide a frequency response output that in comparison to the frequency response of the first piezoelectric device is indicative for the presence of hydrogen gas.

11. A hydrogen gas sensor according to claim 10, wherein the piezoelectric devices are quartz microbalances, including a first quartz microbalance having a palladium electrode coating thereon, and a second quartz microbalance having a gold electrode coating thereon.

12. A hydrogen gas sensor according to claim 1, which is sensitive to hydrogen at a concentration of from 0% to 100% by volume hydrogen in fluid contacted with said metal layer.

13. A hydrogen gas sensor according to claim 1, which is sensitive for hydrogen in air and in inert atmospheres.

14. A hydrogen gas sensor according to claim 1, wherein said means for outputting the frequency response change indicative of the presence of hydrogen gas comprises an electronics module coupled to the piezoelectric device.

15. A hydrogen gas sensor according to claim 1, wherein said means for outputting the frequency response change indicative of the presence of hydrogen gas comprises an alarm.

16. A hydrogen gas sensor according to claim 1, wherein said means for outputting the frequency response change indicative of the presence of hydrogen gas comprises a visual display.

17. A method of determining the presence of hydrogen gas in an environment, comprising contacting gas from the environment with a piezoelectric device including a hydrogen-interactive metal which in exposure to hydrogen gas provides an altered frequency response relative to corresponding operation when the environment contains no hydrogen gas.

18. A method according to claim 17, further comprising monitoring the frequency response characteristic of the piezoelectric device.

19. A method according to claim 18, further comprising generating an output indicative of the presence of hydrogen in the environment from the monitored frequency response characteristic of the piezoelectric device.

20. A method according to claim 17, wherein said environment is an inert gas environment.

21. A method according to claim 17, wherein said environment comprises air.

22. A method according to claim 17, wherein the hydrogen-interactive metal comprises one or more metal species selected from the group consisting of nickel, palladium, platinum, cobalt, rhodium, iridium, iron, ruthenium, and osmium, alloys of two or more of the foregoing metal species, and alloys containing one or more of the foregoing metal species with other metal species.

23. A method according to claim 17, wherein the hydrogen-interactive metal comprises one or more metal species selected from the group consisting of palladium, platinum, nickel, alloys of two or more of the foregoing metals, and alloys containing one or more of the foregoing metals with other metal species.

24. A method according to claim 17, wherein the hydrogen-interactive metal comprises palladium.

25. A method according to claim 17, wherein the piezoelectric device comprises a surface acoustic wave device.

26. A method according to claim 17, wherein the thickness of the hydrogen-interactive metal is from about 10 to about 100,000 Å.

27. A method according to claim 17, wherein the thickness of the hydrogen-interactive metal is from about 20 to about 2000 Å.

28. A method of determining the presence of hydrogen gas in an environment, comprising contacting gas from the environment with a quartz microbalance having a palladium electrode coating which is hydrogen-interactive and in exposure to hydrogen gas provides an altered frequency response relative to corresponding operation when the environment contains no hydrogen gas.

29. A method according to claim 17, further comprising a second piezoelectric device of corresponding type but lacking the hydrogen-interactive metal, and constructed and arranged to provide a frequency response output that in comparison to frequency response output of the first piezoelectric device is indicative of the presence of hydrogen gas.

30. A method according to claim 29, wherein the piezoelectric devices comprise quartz microbalances, including a first quartz microbalance having a palladium electrode coating thereon, and a second quartz microbalance having a gold electrode coating thereon.

31. A hydrogen gas sensor, comprising:
a piezoelectric device that is arranged for contacting gas from a monitored environment to detect the presence of hydrogen therein and that is electrically excitable to exhibit a frequency response;
a metal layer on a surface of the piezoelectric device that in exposure to hydrogen gas reversibly interacts therewith to change the frequency response of the piezoelectric device; and
means for outputting the frequency response change indicative of the presence of hydrogen gas,
wherein the piezoelectric device comprises a quartz microbalance including an electrode coating comprising said metal layer.

32. A hydrogen gas sensor, comprising:
a piezoelectric device that is electrically excitable to exhibit a frequency response;
a metal layer about 50 to 500 Å thick on a surface of the piezoelectric device that in exposure to hydrogen gas reversibly interacts therewith to change the frequency response of the piezoelectric device; and
means for outputting the frequency response change indicative of the presence of hydrogen gas.

33. A method of determining the presence of hydrogen gas in an environment, comprising contacting gas from the environment with a quartz microbalance including an electrode formed from the hydrogen-interactive metal which in exposure to hydrogen gas provides an altered frequency response relative to corresponding operation when the environment contains no hydrogen gas.

34. A method of determining the presence of hydrogen gas in an environment, comprising contacting gas from the environment with a piezoelectric device including a hydrogen-interactive metal from about 50 to about 500 Å thick, which in exposure to hydrogen gas provides an altered frequency response relative to corresponding operation when the environment contains no hydrogen gas.

35. A hydrogen gas sensing apparatus, comprising a piezoelectric device arranged for contacting gas from a monitored environment, said piezoelectric device being electrically excitable to exhibit a frequency response and having a metal layer on a surface of said piezoelectric device which, upon exposure to hydrogen gas, reversibly selectively interacts therewith to change the frequency response of the piezoelectric device without hysteresis effects, and said piezoelectric device providing an altered frequency response relative to reference conditions corresponding to operation when the monitored environment contains no hydrogen gas.

36. A method of sensing hydrogen gas in a monitored environment, comprising providing a piezoelectric device according to claim 35, and monitoring the frequency response of said piezoelectric device to determine the presence of hydrogen gas in said monitored environment.

* * * * *

UNITED STATES PATENT AND TRADEMARK OFFICE
CERTIFICATE OF CORRECTION

| | | |
|---|---|---|
| PATENT NO. | : 6,029,500 | Page 1 of 2 |
| APPLICATION NO. | : 09/081957 | |
| DATED | : February 29, 2000 | |
| INVENTOR(S) | : Glenn M. Tom | |

It is certified that error appears in the above-identified patent and that said Letters Patent is hereby corrected as shown below:

Abstract, line 4: after "relative to" insert --reference conditions of sensor operating corresponding to--.
Column 8, line 8: change "bum" to --burn--.
Column 11, line 60: after "reversibly" insert --selectively--.
Column 12, line 30: after "reversibly" insert --selectively--.
Column 12, line 65: change "in an environment" to --in a monitored environment--.
Column 12, line 67: before "hydrogen-interactive" insert --layer of--.
Column 13, line 1: after "gas" insert --in gas mixtures ranging from 0% to 100% hydrogen by volume displays a reversible selective response behavior without hysteresis effects and--.
Column 13, line 1: after "relative to" insert --preference conditions--.
Column 13, line 2: before "operation" insert --to--.
Column 13, line 2: before "environment" insert --monitored--.
Column 13, lines 40-46, claim 28 should read: --A method of determining the presence of hydrogen gas in a monitored environment, comprising contacting gas from the environment with a quartz microbalance having a palladium coating thereon which is hydrogen-interactive and in exposure to hydrogen gas in gas mixtures ranging from 0% to 100% hydrogen by volume displays a reversible selective response behavior without hysteresis effects and provides an altered frequency response relative to reference conditions corresponding to operation when the monitored environment contains no hydrogen gas.--.
Column 14, line 7: after "reversibly" insert --selectively--.
Column 14, line 21: after "reversibly" insert --selectively--.
Column 14, line 26: change "in an environment" to --in a monitored environment--.
Column 14, line 28: change "from the hydrogen-interactive" to --from a hydrogen interactive--.
Column 14, line 29: after "gas" insert --in gas mixtures ranging from 0% to 100% hydrogen by volume displays a reversible selective response behavior without hysteresis effects and--.
Column 14, line 30: should read --response relative to reference conditions corresponding to operation when the monitored envi- --.
Column 14, line 33: change "in an environment" to --in a monitored environment--.
Column 14, line 35: after "metal" insert --thereon--.
Column 14, line 36: after "gas" insert --in gas mixtures ranging from 0% to 100% hydrogen by volume displays a reversible selective response behavior without hysteresis effects and--.
Column 14, line 37: after "relative to" insert --reference conditions--.
Column 14, line 37: after "corresponding" insert --to--.

UNITED STATES PATENT AND TRADEMARK OFFICE
CERTIFICATE OF CORRECTION

PATENT NO. : 6,029,500
APPLICATION NO. : 09/081957
DATED : February 29, 2000
INVENTOR(S) : Glenn M. Tom It is certified that error appears in the above-identified patent and that said Letters Patent is hereby corrected as shown below:

Column 14, line 38: before "environment" insert --monitored--.

Signed and Sealed this

Seventh Day of August, 2007

JON W. DUDAS
*Director of the United States Patent and Trademark Office*